United States Patent
Blatchford et al.

(10) Patent No.: US 6,461,467 B2
(45) Date of Patent: Oct. 8, 2002

(54) MEDICAL DRESSINGS WITH MULTIPLE ADHESIVES AND METHODS OF MANUFACTURING

(75) Inventors: Todd A. Blatchford, Woodbury, MN (US); Steven B. Heinecke, New Richmond, WI (US); Donald H. Lucast, North St. Paul; Donald G. Peterson, Shoreview, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/840,405

(22) Filed: Apr. 23, 2001

(65) Prior Publication Data

US 2001/0051178 A1 Dec. 13, 2001

Related U.S. Application Data

(62) Division of application No. 09/524,139, filed on Mar. 10, 2000.

(51) Int. Cl.[7] ............................ B44C 3/02; B32B 31/20; B05D 1/32; A61L 15/58; A61F 13/02
(52) U.S. Cl. ..................... 156/230; 156/234; 156/240; 156/241; 156/247; 156/250; 156/289; 156/293; 427/2.31; 427/282; 428/42.3; 428/195; 428/914; 424/445; 424/448; 602/43; 602/55; 602/58
(58) Field of Search ................... 156/230, 234, 156/235, 240, 241, 247, 250, 289, 293, 298; 427/2.21, 2.31, 272, 282, 146; 428/41.8, 41.9, 42.3, 195, 202, 914, 343; 424/443, 445, 448; 602/43, 55, 57, 58

(56) References Cited

U.S. PATENT DOCUMENTS 1,280,631 A   10/1918   Atkinson
RE24,906 E    12/1960   Ulrich
3,389,827 A    6/1968   Abere et al.

(List continued on next page.)

FOREIGN PATENT DOCUMENTS

EP   0 035 399 B1    2/1985
EP   0 051 935 B1   11/1986

(List continued on next page.)

OTHER PUBLICATIONS

Satas, D., Ed., *Handbook of Pressure Sensitive Adhesive Technology*, Ch. 18, Van Nostrand Reinhold Co., Title Page, Publication Page, Table of Contents, and pp. 384–403 (1982).

*Primary Examiner*—J. A. Lorengo
(74) *Attorney, Agent, or Firm*—John A. Burtis

(57) ABSTRACT

Medical dressings are disclosed that include multiple exposed pressure sensitive adhesives. One of the pressure sensitive adhesives includes a bioactive agent and is substantially contact transparent. In some embodiments, all of the adhesives are substantially contact transparent. Also provided are methods of manufacturing the medical dressings. By providing multiple exposed pressure sensitive adhesives, the pressure sensitive adhesive formulations can be varied to provide desired properties in different areas of the dressing. A pressure sensitive adhesive that exhibits relatively high tack to skin may be provided around the periphery of the dressing while a pressure sensitive adhesive incorporating a bioactive agent is provided in the center of the dressing. Alternatively, a higher tack pressure sensitive adhesive may be provided at two opposing sides of the dressing with a bioactive adhesive located in between the opposing portions of higher tack adhesive. The present invention also provides methods of transferring adhesives using a mask such that the adhesive is transferred to selected areas of a receiving surface. The mask may be provided in the form of a liner including a plurality of voids formed therein.

37 Claims, 4 Drawing Sheets

U.S. PATENT DOCUMENTS

| | | | |
|---|---|---|---|
| 3,645,835 A | 2/1972 | Hodgson | |
| 4,112,213 A | 9/1978 | Waldman | |
| 4,263,085 A | 4/1981 | Ellis | |
| 4,310,509 A | 1/1982 | Berglund et al. | |
| 4,323,557 A | 4/1982 | Rosso et al. | |
| 4,385,588 A | 5/1983 | Bennetot | |
| 4,472,780 A | 9/1984 | Chenoweth et al. | |
| 4,537,647 A | * 8/1985 | Foster | 156/245 |
| 4,579,616 A | 4/1986 | Windischmann et al. | |
| 4,595,001 A | 6/1986 | Potter et al. | |
| 4,655,868 A | 4/1987 | Hefele | |
| 4,668,602 A | 5/1987 | Hosaka et al. | |
| 4,737,410 A | 4/1988 | Kantner | |
| 4,759,968 A | 7/1988 | Janssen | |
| 4,762,766 A | 8/1988 | Melbye | |
| 4,791,284 A | 12/1988 | Ludden | |
| 4,795,516 A | 1/1989 | Strand | |
| 4,824,702 A | 4/1989 | Straub | |
| 4,919,994 A | 4/1990 | Incremona et al. | |
| 4,931,282 A | 6/1990 | Asmus et al. | |
| 4,952,618 A | 8/1990 | Olsen | |
| 4,999,076 A | 3/1991 | Incremona et al. | |
| 5,088,483 A | 2/1992 | Heinecke | |
| 5,160,315 A | 11/1992 | Heinecke et al. | |
| 5,160,615 A | 11/1992 | Heinecke et al. | |
| 5,276,079 A | 1/1994 | Duan et al. | |
| 5,344,681 A | 9/1994 | Calhoun et al. | |
| 5,391,249 A | 2/1995 | Senft | |
| 5,449,540 A | 9/1995 | Calhoun et al. | |
| 5,520,629 A | 5/1996 | Heinecke et al. | |
| 5,531,855 A | 7/1996 | Heinecke et al. | |
| 5,614,310 A | 3/1997 | Delgado et al. | |
| 5,622,711 A | 4/1997 | Chen | |
| 5,633,010 A | 5/1997 | Chen | |
| 5,681,413 A | 10/1997 | Hille et al. | |
| 5,702,753 A | 12/1997 | Yasis et al. | |
| 5,713,842 A | 2/1998 | Kay | |
| 5,730,823 A | 3/1998 | Donat | |
| 5,738,642 A | 4/1998 | Heinecke et al. | |
| 5,741,387 A | * 4/1998 | Coleman | 156/240 |
| 5,772,329 A | 6/1998 | Bardon et al. | |
| 5,776,283 A | 7/1998 | Kato | |
| 5,849,325 A | 12/1998 | Heinecke et al. | |
| 5,908,693 A | 6/1999 | Delgado et al. | |
| 6,136,128 A | * 10/2000 | Chung | 156/235 |

FOREIGN PATENT DOCUMENTS

| | | |
|---|---|---|
| EP | 437 944 B1 | 7/1991 |
| EP | 465 023 B1 | 1/1992 |
| GB | 1280631 | 7/1972 |

* cited by examiner

MEDICAL DRESSINGS WITH MULTIPLE ADHESIVES AND METHODS OF MANUFACTURING

This is a division of application Ser. No. 09/524,139, filed Mar. 10, 2000, (pending), which is incorporated herein by reference.

FIELD OF THE INVENTION

The present invention generally relates to adhesive medical dressings. More particularly, the present invention provides a medical dressing with multiple exposed adhesives, one of which includes a bioactive agent. The present invention also provides a masked adhesive transfer process.

BACKGROUND

The use of transparent film dressings continues to grow at an accelerated rate. In addition to their use as protective layers over wounds, where they facilitate healing in a moist environment while acting as a barrier to contaminating liquids and bacteria, the films are also used over catheters to prevent contamination of the catheter insertion site by contaminating liquids and bacteria. Dressings fitting the above description are available under a number of trade names such as TEGADERM™ (3M Company, St. Paul, Minn.), BIOCLUSIVE™ (Johnson & Johnson Company, New Brunswick, N.J.), and OP-SITE™ (T. J. Smith & Nephew, Hull, England).

The adhesives used to secure the dressings in place on a patient are typically fairly aggressive, i.e., the adhesives have a high tack, to prevent unwanted release from a wound edge or catheter site. Many of the adhesives are also contact transparent to allow visual monitoring of wounds or catheter sites without removing the dressings.

One of the purposes of the dressings is to reduce or prevent infection of wounds or catheter sites. Attempts have been made to include antimicrobial agents in dressings to further improve the ability of dressings to reduce or prevent infection by reducing migration of infectious agents across the dressing surfaces. These attempts typically have significant drawbacks.

One approach to incorporating antimicrobial agents in medical dressings involves the inclusion of a pad that acts as a carrier for the antimicrobial agent. The pads, however, typically prevent visual monitoring of the wound or catheter site located directly beneath the pad. The pads are also typically not adhesive, i.e., they cannot adhere to the wound or catheter site. As a result, the dressing is not as firmly secured as a similar dressing that does not include a pad.

Other approaches have involved incorporating antimicrobial agents directly into the pressure sensitive adhesive used on a dressing, but this approach also suffers from drawbacks. For example, in those pressure sensitive adhesives that provide desired levels of tack to a patient's skin (to, e.g., prevent edge lift off of the dressing), the antimicrobial agents are also bound so well that they are not available in effective concentrations at the wound or catheter site.

Pressure sensitive adhesive formulations incorporating antimicrobial agents that are available in effective concentrations at a wound or catheter site are known. See, e.g., U.S. Pat. Nos. 5,614,310 and 5,908,693 (both to Delgado et al.). These pressure sensitive adhesives, however, exhibit tack to skin that is reduced upon exposure to moisture such as, e.g., sweat, when in place on a patient. As a result, these pressure sensitive adhesives do not present good candidates for use as the only adhesive exposed on, e.g., medical dressings that require relatively high tack to reduce the likelihood of unwanted removal.

SUMMARY OF THE INVENTION

The present invention provides medical dressings that include multiple exposed pressure sensitive adhesives. One of the pressure sensitive adhesives includes a bioactive agent and is substantially contact transparent. It may also be preferred that all of the adhesives are substantially contact transparent.

Also provided are methods of manufacturing the medical dressings. By providing multiple exposed pressure sensitive adhesives, the pressure sensitive adhesive formulations can be varied to provide desired properties in different areas of the dressing. For example, one of the exposed pressure sensitive adhesives may exhibit relatively high tack to skin while another exposed pressure sensitive adhesive may serve as a vehicle for a bioactive agent while still providing some adhesive properties.

The term "substantially contact transparent," as used in connection with the present invention, means that, when adhered to a patient's skin, a wound or catheter site can be visually monitored through those portions of the backing and pressure sensitive adhesive or adhesives in contact with the patient's skin without requiring removal of the dressing. The term "bioactive agent," as used in connection with the present invention, includes pharmacologically active ingredients, such as drugs, antibiotic agents, antimicrobial agents, etc.

In some embodiments, a pressure sensitive adhesive that exhibits relatively high tack to skin may be provided around the periphery of the dressing while a pressure sensitive adhesive incorporating a bioactive agent is provided in the center of the dressing. As a result, the edges of the dressing can be firmly secured to a patient, while the center of the dressing provides, e.g., a degree of infection control if the bioactive agent is antimicrobial. In other embodiments, a higher tack pressure sensitive adhesive may be provided at two opposing sides of the dressing with a bioactive adhesive located in between the opposing portions of higher tack adhesive.

The different adhesives may be applied directly to different areas of the dressing backing such that different areas of the backing include only one pressure sensitive adhesive. Alternatively, one or more of the pressure sensitive adhesives may be provided over one or more pre-applied areas of pressure sensitive adhesive such that the pressure sensitive adhesives are located in multiple layers over a portion of the dressing. In all cases, however, at least two different pressure sensitive adhesives are exposed on the bottom surface of the dressing. It is further preferred that all of the pressure sensitive adhesives are moisture vapor permeable and/or provided using techniques (e.g., pattern coating) that provide a desired level of moisture vapor permeability.

The present invention also provides methods of transferring adhesives using a mask such that the adhesive is transferred to selected areas of a receiving surface. The mask may be provided in the form of a liner including a plurality of voids formed therein. This method can provide precise control over registration of the transferred adhesive on the receiving surface, e.g., a backing. Registration control may be particularly important if the adhesive is transferred to, e.g., a backing and carrier composite including windows to facilitate delivery of the backing. In such a situation, it may be desirable to accurately register the transferred adhesive with, e.g., the windows in the carrier. Examples of such dressings are found in, e.g., U.S. Pat. No. 5,531,855 (Heinecke et al.).

In one aspect, the present invention provides a medical dressing having top and bottom surfaces, the medical dressing including a substantially contact transparent backing; a first pressure sensitive adhesive exposed on the bottom surface of the dressing; and a second pressure sensitive adhesive exposed on the bottom surface of the dressing, wherein the second pressure sensitive adhesive includes at least one bioactive agent and is substantially contact transparent.

In another aspect, the present invention provides a method of manufacturing a medical dressing having top and bottom surfaces by providing a substantially contact transparent backing; providing a first pressure sensitive adhesive that is exposed on the bottom surface of the dressing; and providing a second pressure sensitive adhesive that is exposed on the bottom surface of the dressing, wherein the second pressure sensitive adhesive includes at least one bioactive agent and is substantially contact transparent.

In another aspect, the present invention provides a method of transferring an adhesive to a substrate by providing a mask liner including a plurality of voids formed therein; locating a receiving surface proximate a first side of the mask liner, wherein at least a portion of the receiving surface is exposed through at least one of the plurality of voids in the mask liner; providing transfer adhesive on a transfer liner; and transferring at least a portion of the transfer adhesive to the portion of the receiving surface exposed through the void in the mask liner.

These and other features and advantages of the articles and methods of the present invention are discussed below.

DETAILED DESCRIPTION OF ILLUSTRATIVE EMBODIMENTS OF THE INVENTION

Figure 1:
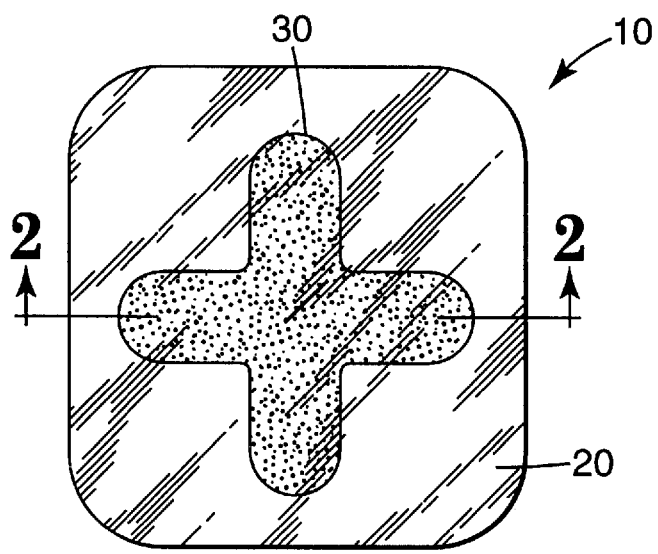
FIG. 1 is a plan view of the adhesive surface of one medical dressing according to the present invention.

The present invention is particularly useful in the field of pressure sensitive adhesive medical dressings having high moisture vapor permeable film backings. Issued U.S. Pat. No. 3,645,835 and European Patent Application Publication No. 0 437 944 describe methods of making such films and methods for testing their permeability. Preferably, the film/adhesive composite dressings should transmit moisture vapor at a rate equal to or greater than human skin. In one aspect, the adhesive coated film may advantageously transmit moisture vapor at a rate of at least 300 g/m$^2$/24 hrs/37° C./100–10% RH, more preferably at least 700 g/m$^2$/24 hrs/37° C./100–10% RH, and most preferably at least 2000 g/m$^2$/24 hrs/37° C./100–10% RH using the inverted cup method as described in U.S. Pat. Nos. 3,645,835 and 5,849,325.

The backing film is also preferably conformable to anatomical surfaces. As such, when the backing is applied to an anatomical surface, it conforms to the surface even when the surface is moved. The preferred backing is also conformable to anatomical joints. When the joint is flexed and then returned to its unflexed position, the backing stretches to accommodate the flexion of the joint, but is resilient enough to continue to conform to the joint when the joint is returned to its unflexed condition. A description of this characteristic of backings preferred for use with the present invention can be found in U.S. Pat. Nos. 5,088,483 and 5,160,315.

A description of some backings that may be preferred for use in the medical dressings of the present invention can be found in issued U.S. Pat. Nos. 5,088,483 and 5,160,315, as well as European Patent Application Publication No. 0 437 944.

Particularly preferred film backings may be selected from the group of elastomeric polyurethane, copolyester, or polyether block amide films, or combinations thereof. These films combine the desirable properties of resiliency, high moisture vapor permeability, and transparency that may be preferred in the backings. Also, although the backings are depicted below as monolayer articles, it will be understood that they could include multiple layers as described in, e.g., European Patent Application Publication No. 0 437 944.

Pressure sensitive adhesives that can be used in the medical dressings of the present invention include adhesives that are preferably compatible with human or animal skin, more preferably those that are of the class known as "hypoallergenic" adhesives. Examples of some adhesives useful in connection with the invention include, but are not limited to the acrylate copolymers described in U.S. Pat. No. RE 24,906, particularly a 97:3 iso-octyl acrylate:acrylamide copolymer. Also useful is an 70:15:15 isooctyl acrylate:ethyleneoxide acrylate:acrylic acid terpolymer, as described in U.S. Pat. No. 4,737,410 (see Example 31). Other useful adhesives are described in U.S. Pat. Nos. 3,389,827; 4,112,213; 4,310,509; and 4,323,557; as well as UK Patent No. 1280631 (see, e.g., polyvinyl ether adhesives) and European Patent Nos. 35399 and 51935. Some useful pressure sensitive adhesives may include bioactive agents as described in, e.g., U.S. Pat. Nos. 4,310,509; 4,323,557; 5,614,310; and 5,908,693. Some preferred bioactive agents may be antimicrobial agents to enhance wound or catheter site infection control.

The layer or layers of pressure sensitive adhesives located on the backings of the medical dressings of the invention preferably transmit moisture vapor at a rate greater than or equal to that of human skin. While such a characteristic can be achieved through the selection of an appropriate adhesive, it is also contemplated in the present invention that other methods of achieving a high relative rate of moisture vapor transmission may be used, such as, e.g., pattern coating the adhesive.

In addition to moisture vapor permeability and hypoallergenicity, it may also be preferred that the adhesives exhibit high initial tack upon application to the skin or the surface of a nail. One such pressure sensitive adhesive is described in U.S. Pat. No. 5,849,325, and other useful adhesives may include polyvinyl ether adhesives as discussed in, e.g., UK Patent No. 1280631. One advantage of an adhesive exhibiting high initial tack is additional securing of, e.g., a catheter by the dressing may be more quickly enhanced as opposed to adhesives that have a lower initial tack.

The medical dressings of the present invention may also include a low adhesion coating on the backing, which may be preferably coated as a solution of polyvinyl N-octadecyl carbamate and a blend of silicone resins, as described in, e.g., U.S. Pat. No. 5,531,855. While it may be preferred that the medical dressings of the present invention include a low adhesion coating, medical dressings without such a coating are also considered to be within the scope of the present invention.

When provided as a part of the medical dressing (before delivery), suitable liners are available from a variety of manufacturers in a wide variety of proprietary materials. Those skilled in the art will normally test those liners in simulated use conditions against an adhesive of choice to arrive at a product with the desired release characteristics. The materials used to supply the liners for the flexible film dressings manufactured according to the present invention are preferably substantially more rigid than the backing film.

Figure 2:
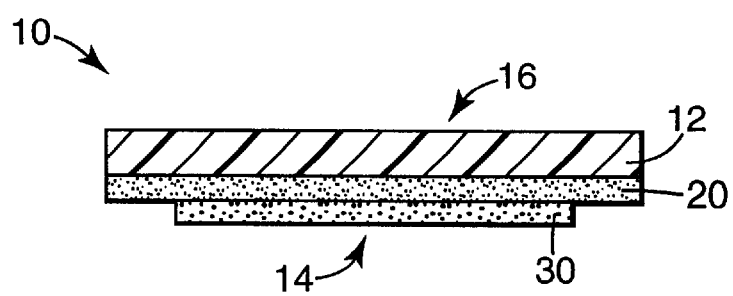
FIG. 2 is a cross-sectional view of the dressing of FIG. 1, taken along line 2—2 in FIG. 1.

FIGS. 1 and 2 depict an illustrative embodiment of one medical dressing according to the present invention. The dressing 10 has a backing 12, a bottom surface 14 and a top surface 16. The bottom surface 14 of the dressing is that surface that is designed to face the patient when the dressing 10 is applied and is typically the surface of the dressing on which any pressure sensitive adhesives used to secure the dressings 10 are exposed. The backing 12 is preferably a polymeric film that is substantially contact transparent.

Two different pressure sensitive adhesives 20 and 30 are exposed on the bottom surface 14 of the dressing 10. In the illustrated embodiment, a first adhesive 20 is exposed over a portion of the bottom surface 14 of the dressing 10 while a second adhesive 30 is exposed over a second portion of the bottom surface 14. The second adhesive 30 may preferably include at least one bioactive agent.

As shown in the dressing 10, it may be preferred that the second adhesive 30 be exposed within a distinct area on the bottom surface 14 of the dressing 10. It may also be preferred that the first adhesive 20 be located about the perimeter of the bottom face 14, more preferably substantially the entire perimeter of the bottom face 14. In other words, it may be preferred that the first adhesive 20 form a border around the bottom face 14 of the backing 12.

One potential and possibly preferred difference between the first adhesive 20 and the second adhesive 30 (which contains a bioactive agent) is that the tack of the first adhesive 20 on the skin or nail of a patient may be higher than the tack of the second adhesive 30. In other words, the adhesive bond formed between the first adhesive 20 and a patient is stronger than the bond formed between the second adhesive 30 and the patient. One potential advantage of using adhesives with different tack is that, where the first adhesive 20 located in a border around the second adhesive 30 or on opposing ends of the dressing (see, e.g., FIG. 4A), the backing may be more firmly secured to the patient. That may prevent or reduce inadvertent lift-off of the edges of the dressings.

It may also be preferred that the second adhesive 30 form a desired shape. One example of a desired shape is illustrated in FIG. 1, where the second adhesive 30 forms a cross pattern on the bottom face 14 of the backing 12. In instances where the different adhesives can be visually distinguished from each other, the pattern formed by the adhesives 20 and 30 may assist in accurate placement of the second adhesive 30 over a desired location on a patient. In some instances, it may be desirable to provide a colorant as a part of the adhesives or the backing (or otherwise) to further assist in placement of the dressing 10. In other instances, the constituents in the adhesive may exhibit a color without the addition of colorants.

The cross-sectional view of the dressing 10 also depicts that, in the illustrated embodiment, the first pressure sensitive adhesive 20 is located over substantially all of the bottom surface 14 of the dressing 10. Where the second pressure sensitive adhesive 30 is found, it is located over the first adhesive 20. As a result, the second pressure sensitive adhesive 30 may not have any direct contact with the backing 12. The first pressure sensitive adhesive 20 is exposed in those areas where the second pressure sensitive adhesive 30 is not found.

Figure 3:
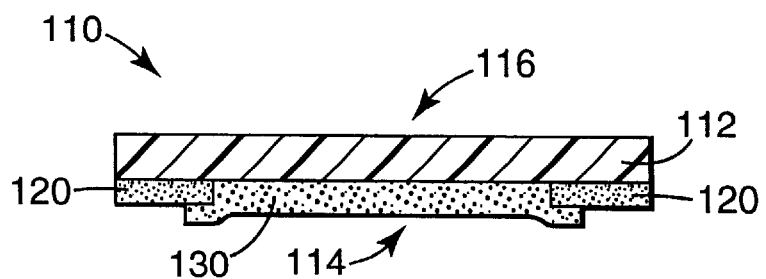
FIG. 3 is a cross-sectional view an alternative dressing.

An alternative dressing construction is depicted in cross-section in FIG. 3. In that embodiment, the first pressure sensitive adhesive 120 is not located over all of the bottom face 114 of the backing 112. Rather, the first pressure sensitive adhesive 120 is provided only on the edges of the backing 112. The second pressure sensitive adhesive 130 can then be located directly on the backing 112, rather than over the first adhesive 120 (as in dressing 10). The two adhesives 120 and 130 may preferably overlap along their edges 122 and 132 as shown to prevent adhesive voids that may negatively impact retention of the dressing 110 on the skin of a patient. Alternatively, the edges of the different adhesives may not overlap.

Figure 4A:
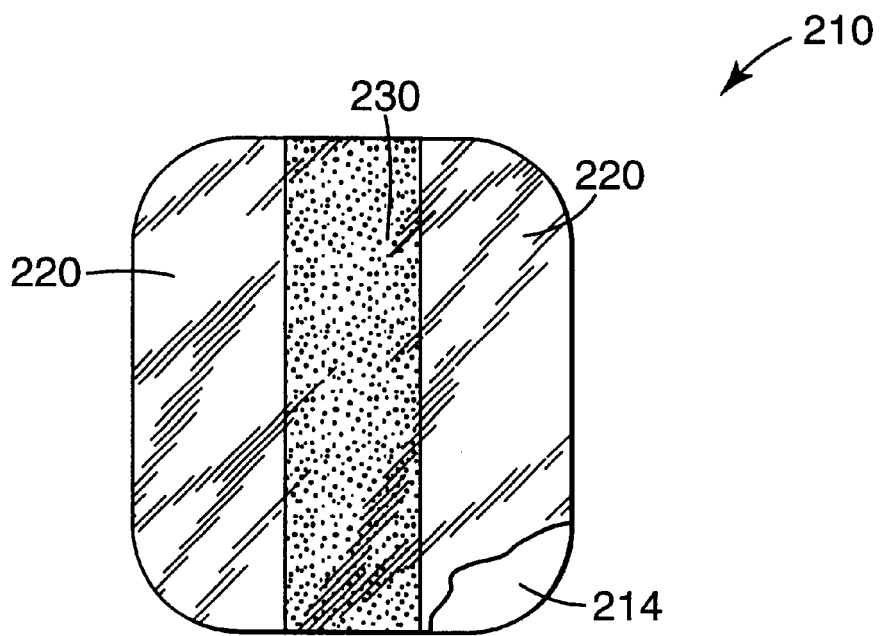
FIGS. 4A and 4B are plan views of the bottom surfaces of alternative medical dressings including multiple exposed pressure sensitive adhesives according to the present invention.

FIG. 4A illustrates an alternative medical dressing 210 with a first pressure sensitive adhesive 220 exposed on opposing sides or edges of the bottom surface 214 of the dressing 210. A strip of a second pressure sensitive adhesive 230 is exposed on the bottom surface 214 of the dressing 210 between the opposing strips of the first pressure sensitive adhesive 220. The exposed strip of second adhesive 230 may preferably be located down the center of the bottom face 214.

Figure 4B:
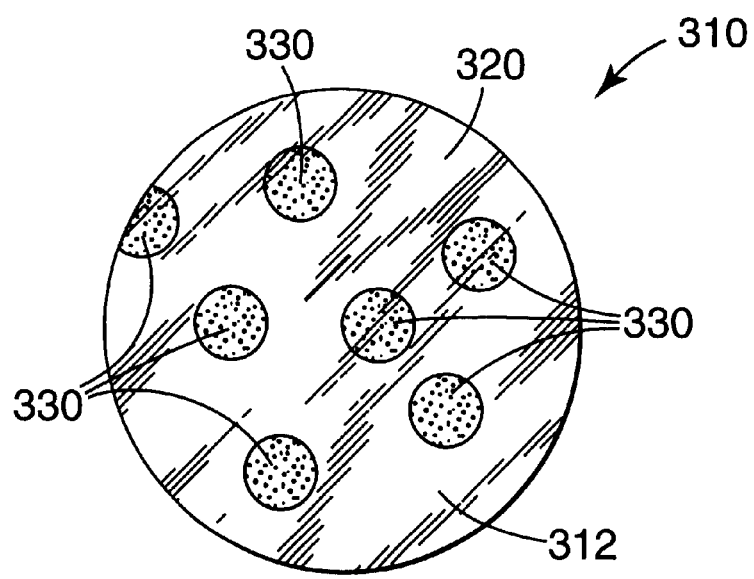

FIG. 4B illustrates another illustrative medical dressing 310 that includes a backing 312 on which a first pressure sensitive adhesive 320 is exposed in certain areas. A second pressure sensitive adhesive 330 is also exposed on the bottom surface of the dressing 310. In contrast to the various embodiments described above, the second pressure sensitive adhesive 330 on the dressing 310 is exposed in a plurality of distinct areas rather than a single distinct area. The size and/or shape of the distinct areas of exposed second pressure sensitive adhesive 330 may be uniform as illustrated in FIG. 4B. Alternatively, the size and/or shape of the distinct areas may vary. Furthermore, the arrangement of the distinct areas may be ordered or random.

Figure 5:
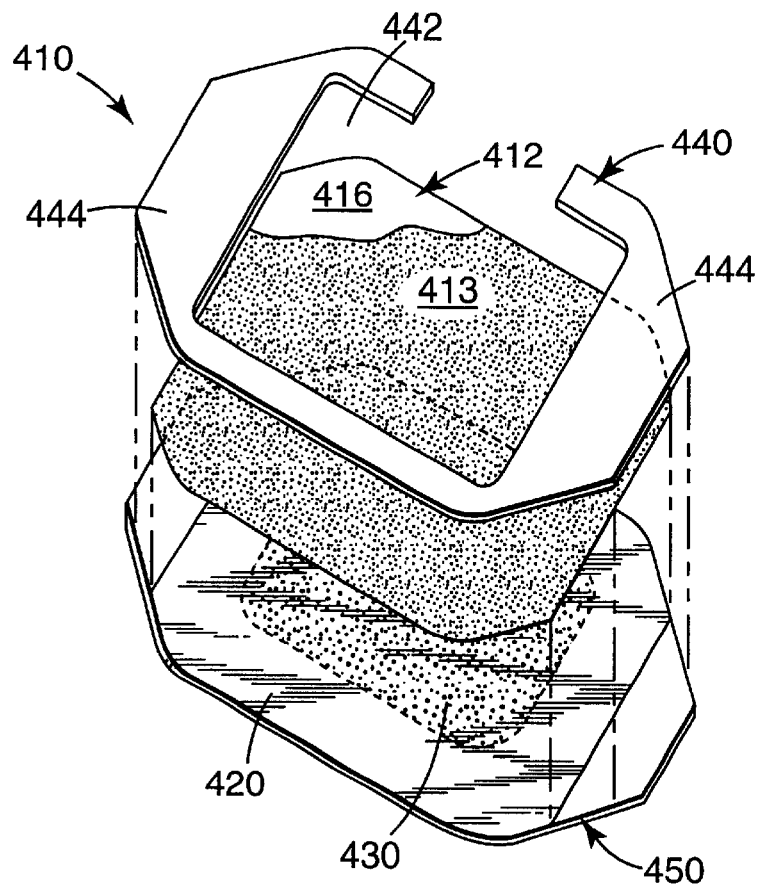
FIG. 5 is an exploded view of one dressing according to the present invention including a carrier frame with a window formed therein.

FIG. 5 illustrates another medical dressing 410 that includes a carrier delivery system. The medical dressing 410 includes a backing 412 that is preferably conformable as described above; first and second pressure sensitive adhesives 420 and 430 that are exposed on the bottom surface of the dressing 410 (although they are depicted as attached to the liner 450 in FIG. 5 for the purposes of illustration only); and a carrier 440 attached to the backing 412. Also depicted in FIG. 5 is a liner 450 that bonds to the exposed portions of the first and second pressure sensitive adhesives 420 and 430 to protect them until the backing 412 is delivered. When the backing 412 used in the medical dressings of the present invention is one of the flexible polymeric films discussed above, it is often desirable to supply a carrier or some other support that is substantially more rigid than the backing 412 to prevent the backing from wrinkling or folding onto itself in whole or in part during application of the dressing 410.

The top face 416 of the backing 412 may also include a low adhesion coating 413 such as that described in, e.g., U.S. Pat. No. 5,531,855, to reduce surface friction between the backing and other objects or surfaces which also reduces unwanted removal of the backing 412 after application to a wearer. It will be understood that the low adhesion coating 413 is optional and that it may or may not be provided.

In FIG. 5, a portion of the carrier 440 is preferably removed creating a window 442 exposing a portion of the top face 416 of the backing 412. It will be understood, however, that in some instances the carrier 440 may not include a window 442, i.e., the carrier 440 may be coextensive with the backing 412.

In those medical dressings 410 in which a window 442 is provided, removal, during manufacturing, of the window portion of the carrier 440 that would normally cover window 442 is optional. Removal does eliminate one step in the delivery process (i.e., the step of removing a portion of the carrier material from the window 442 prior to removing the backing 412 from the liner 450) and reduces the waste stream at the consumer level. However, some customers may prefer that the portion of the carrier 440 normally covering window 442 remain intact until the dressing 410 reaches the end user. The portion of the carrier 440 that remains after window removal preferably extends about at least a substantial portion of the periphery of the backing 412 to support it after removal from the liner 450.

Carrier 440 may also preferably include at least one tab 444 (two are illustrated in FIG. 5) that extends beyond the perimeter of backing 412 to assist in removal of the backing 412 from the liner 450 without contacting the exposed adhesives 420 or 430. It is preferred that the tabs 444 be completely integral with the carrier 440 such that pulling the tab 444 and integral carrier 440 away from the liner 450 results in removal of the carrier 440, backing 412 and adhesives 420 and 430 from the liner 450.

The carrier 440 may preferably be attached to backing 412 (over any low adhesion coating, if provided) with a heat seal bond. Other bonding mechanisms, such as adhesives, mechanical bonds, wax coatings, surface energy attraction, etc. can be used in place of the preferred heat seal bond. Regardless of the type of bonding used to attach the carrier 440 to the backing 412, the bond should be secure, yet releasable, i.e., the carrier 440 and backing 412 can be separated without destroying the integrity of the backing 412 or the bond between the exposed pressure sensitive adhesives 420 and 430 on the backing and the skin of a wearer after application of the backing 412.

If the carrier material 440 is heat-sealable to the backing 412 for the purpose of manufacturing the medical dressings, the carrier 440 may be, e.g., polyethylene/vinyl acetate copolymer-coated papers and polyester films. One example of a preferred heat-sealable carrier material is a polyethylene/vinyl acetate copolymer-coated super calendered Kraft paper (1-80BKG-157 PE; DCP-Lohja, Inc. Westchester, Ill.). Methods and materials conducive to heat sealing are described in U.S. Pat. Nos. 5,531,855 (Heinecke et al.) and 5,738,642 (Heinecke et al.).

The release liner 450 preferably includes a release surface that contacts the exposed pressure sensitive adhesives 420 and 430 when the medical dressing 410 is manufactured. The release surface on the liner 450 is preferably at least coextensive with the exposed pressure sensitive adhesives 420 and 430, but may in some instances be larger (including the entire surface of the liner 450) to simplify manufacturing of the dressings 410. Examples of suitable release materials for use on the release surface include silicones such as UV-9300 and UV-9315 available from GE Silicones, General Electric Company, Waterford, N.Y. The release material would preferably be coated on the release surface at weights sufficient to provide the desired release characteristics to allow removal of the backing 412 when desired.

The release liner 450 itself could be made of kraft papers, polyethylene, polypropylene, polyester or composites of any of these materials. As discussed above, the release surface preferably includes release materials such as fluorochemicals or silicones. For example, U.S. Pat. No. 4,472,480, describes low surface energy perfluorochemical liners. Some preferred liners are papers, polyolefin films, or polyester films coated with silicone release materials. Examples of commercially available silicone coated release papers are POLYSLIK™ silicone release papers available from Rexam Release (Oak Brook, Ill.) and silicone release papers supplied by DCP-Lohja, Inc. (Westchester, Ill.).

Other combinations of adhesives and release materials are contemplated for use with embodiments according to the present invention. Those skilled in the art will be familiar with the processes of testing new combinations of adhesives and release surfaces to arrive at the combination of qualities desired in a final product. The considerations pertinent to the selection of silicone release surfaces can be found in Chapter 18 of the *Handbook of pressure Sensitive Adhesive Technology*, Van Nostrand-Reinhold, 1982, pp. 384–403. U.S. Pat. No. 4,472,480 also describes considerations pertinent to the selection of a perfluoropolyether release liner.

Medical dressings with multiple exposed pressure sensitive adhesives on their bottom surfaces can be manufactured by a variety of processes such as, e.g., screen or roto-gravure printing, of one or more of the pressure sensitive adhesives.

Figure 6:
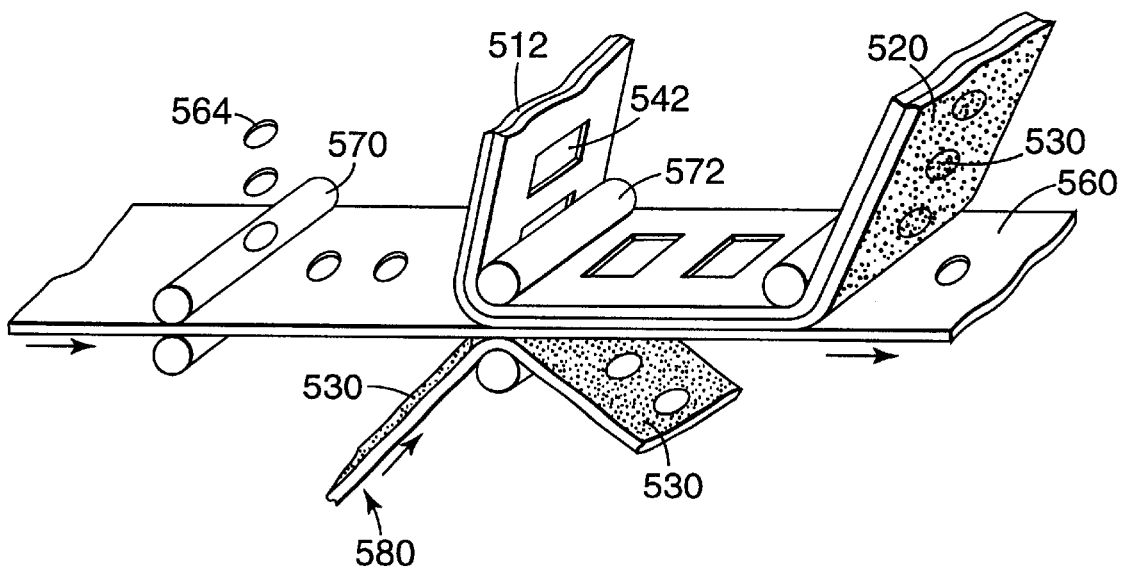
FIG. 6 is a schematic diagram of one process of providing multiple adhesives on a substrate.

FIG. 6 is, however, a schematic diagram of one method of providing multiple exposed adhesives on a substrate, such as, e.g., a backing used in a medical dressing. The methods of providing multiple exposed pressure sensitive adhesives according to the present invention are not limited to the manufacture of adhesive medical dressings. Rather, the methods could be used in any situation in which a pressure sensitive adhesive is desired to be transferred to a receiving surface through voids in a mask liner. The result is that the transferred adhesive can be accurately located and transferred as desired. The transfer method described below relates to medical dressings, although the pressure sensitive adhesive transfer method should not be so limited.

The method includes providing a mask liner 560 that moves through a station 570 in which a pattern of voids 562 are formed. In one method, the voids 562 are formed by die cutting with the removed portions 564 of the liner 560 are removed by, e.g., a vacuum system or any other suitable technique.

The mask liner 560 including the voids 562 is then directed into a transfer station 572 along with a backing 512 that preferably includes a layer of backing adhesive 520 on its bottom surface. The backing 512 preferably also includes a carrier layer 540 attached to the top surface of the backing 512. As discussed above, a carrier 540 may be particularly useful if the backing 512 is a flexible film. Also, it will be understood that the carrier 540 may be laminated to the backing 512 after the transfer station 572. The carrier 540 preferably includes a pattern of windows 542 that are preferably die-cut in the carrier layer 540.

Also directed into the transfer station 572 is a transfer liner 580 that includes a transfer adhesive 530 on the upper surface as shown in FIG. 6. It may be preferred that substantially all of the upper surface of the transfer liner 580 be coated with the transfer adhesive 530. Alternatively, only a portion of the upper surface of the transfer liner 580 may be coated with the transfer adhesive 530 to reduce adhesive waste.

At the transfer station 572, the portion of the transfer adhesive 530 that contacts the backing 512 and backing adhesive 520 composite is transferred thereto. The remainder of the transfer adhesive 530 either remains attached to the transfer liner 580 as shown in FIG. 6 or is transferred to the bottom surface of the mask liner 560.

After removal of the mask liner 560 from contact with the backing adhesive 520 and backing 512, the transfer adhesive 530 remains on the backing adhesive 520 in a pattern that matches the pattern of voids in the mask liner 560.

Figure 7:
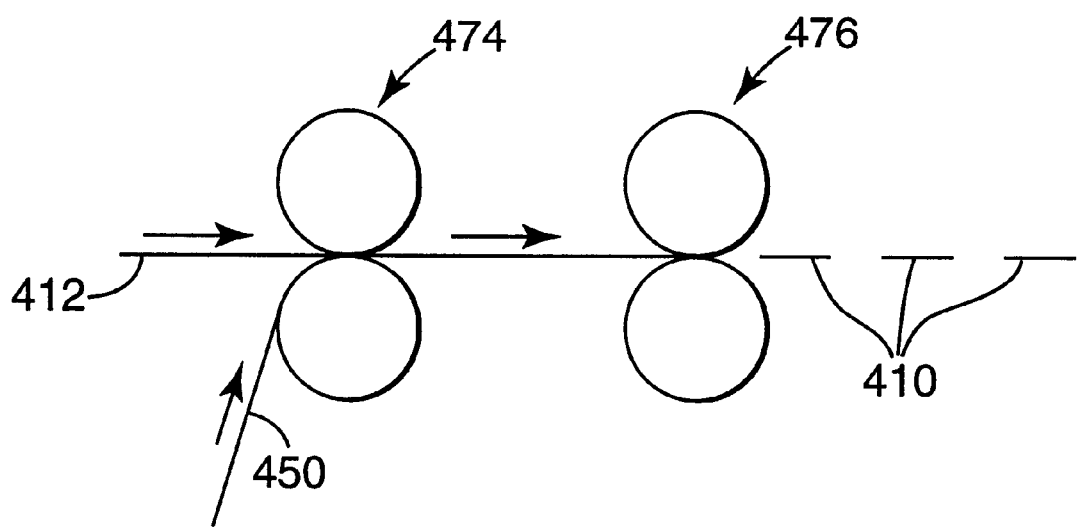
FIG. 7 is a schematic diagram of a process for laminating a liner and forming discrete products using the substrate and adhesives of FIG. 6.
Figure 3:
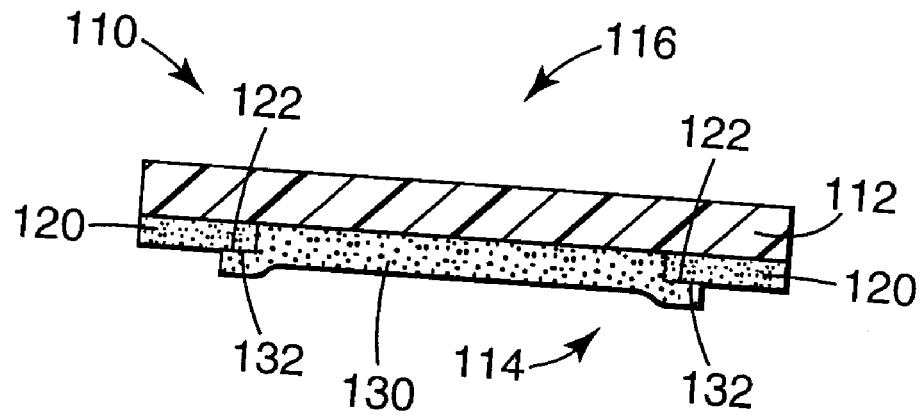
Figure 6:
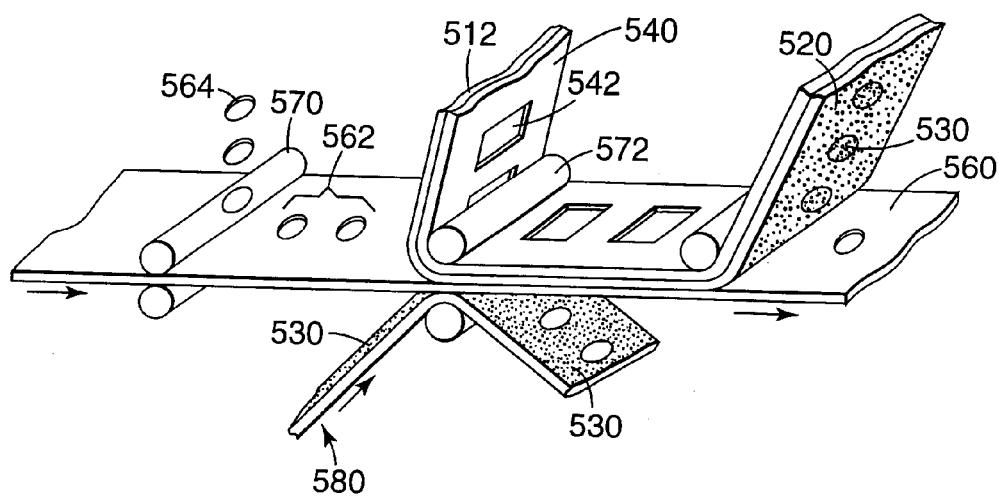
Figure 7:
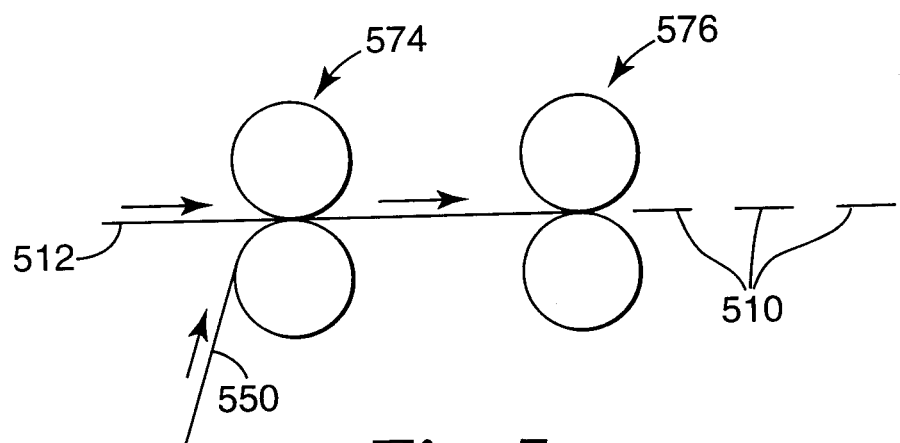

FIG. 7 illustrates another process in which the product of the process depicted in FIG. 6, i.e., the backing 512, backing adhesive 520 and transfer adhesive 530, are mated to a product liner 550 at a liner station 574. Following lamination of the liner 550 to the backing 512 using adhesives 520 and 530, the web can be sheeted or otherwise separated at, e.g., a sheeting station 576 to form dressings 510.

One advantage of using a die-cut mask liner 560 through which the transfer adhesive 530 is transferred is that registration can be maintained between the voids 562 in the mask liner 560 and any features provided in one or more of the backing 512, backing adhesive 520, and carrier 540. Registration control is provided because all of the features are formed in controllable die-cut operations.

Another advantage is that if the transfer adhesive 530 is not amenable to other processes of providing discrete patterns of adhesive such as, e.g., printing or other processes, it may transfer cleanly in a process using a mask liner with voids.

Although various illustrative embodiments of dressings and methods of manufacturing the same have been described above, it should be understood that additional variations are possible. As one example, additional components may be added to the medical dressings, such as the catheter support strips discussed in U.S. Pat. No. 5,520,629.

EXAMPLES

The features and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

EXAMPLE 1

Medical Dressing Preparation Using Rotary Screen Printer

A medical dressing including a transparent film backing, a first pressure-sensitive adhesive, and a second pressure-sensitive adhesive containing an antimicrobial agent was constructed using a rotary screen printer according to the following procedure.

An antimicrobial microsphere adhesive was prepared by mixing together the following ingredients:

1. adhesive microspheres (1217 g) prepared as described in U.S. Pat. No. 5,614,310 (Delgado, et al.) and including (prior to polymerization) isooctyl acrylate (90 parts), N-vinylpyrrolidone (5 parts), and poly(ethylene oxide) acrylate (5 parts);
2. poly(N-vinylpyrrolidone) (121.7 g, K90, ISP Technologies, Inc., Wayne, N.J.);
3. glycerol (334.8 g, Dow Chemical Co., Midland, Mich.); and
4. 20% aqueous chlorhexidine gluconate (CHG) solution (334.8 g, Xttrium Laboratories, Chicago, Ill.).

The antimicrobial microsphere adhesive was coated using a rotary screen printer (available from Stork, Charlotte, N.C.) through a 60-mesh screen as a 2.54 cm stripe on a silicone-coated release liner and dried at 82° C. The dried adhesive thickness was 0.1–0.4 mil (2.5–10 microns). Similarly, the adhesive was coated through a 40-mesh screen with patterns in the form of 5.1 cm diameter circles and 2.54 cm squares. The adhesive thickness of the latter patterns was 1.7–2.0 mil (43–50 microns).

Individual adhesives were transferred by hand to TEGADERM™ transparent dressings (3M Company, St. Paul, Minn.) by cutting out a portion of the dressing liner slightly larger than the pattern and applying the adhesive pattern to the adhesive face of the dressing with light finger pressure.

EXAMPLE 2

Medical Dressing Preparation Using Mask Transfer Liner

A medical dressing including a transparent film backing, a first pressure-sensitive adhesive, and a second pressure-sensitive adhesive containing an antimicrobial agent was constructed using manufacturing equipment and a mask transfer liner according to the following procedure.

A primary adhesive web was prepared as described in Example 1 of U.S. Pat. No. 5,160,315 (Heinecke, et al.). The web included a 0.8 -mil (20 -micron) polyurethane film laminated to an adhesive [isooctyl acrylate/acrylamide (97/3 weight ratio) copolymer] coated differential release liner made of two-side silicone coated paper.

An antimicrobial microsphere adhesive was prepared by mixing together the following ingredients:

1. adhesive microspheres (100 g) prepared as described in U.S. Pat. No. 5,614,310 (Delgado, et al.) and including (prior to polymerization) isooctyl acrylate (90 parts), N-vinylpyrrolidone (5 parts), and poly(ethylene oxide) acrylate (5 parts);
2. poly(N-vinylpyrrolidone) (4 g, K90, BASF);
3. glycerol (5.5 g, Aldrich, Milwaukee, Wis.);
4. 20% aqueous chlorhexidine gluconate (CHG) solution (9.6 g, Xttrium Laboratories, Chicago, Ill.);
5. sorbitol (5.5 g, Lonza Group, Fairlawn, N.J.); and
6. SILWET L-77 (0.8722 g, OSI Specialties, Friendly, W. Va.).

A transfer adhesive web was prepared by coating the antimicrobial adhesive described above at 25 g/m² on the "tight side" of a differential release liner made of two-side silicone coated paper to form the transfer adhesive web.

A mask transfer liner manufactured of bleached Kraft paper (one side polyethylene coated followed by silicone coated and the other side untreated) was die cut to form a series of voids along the center of the liner.

A medical dressing was constructed by laminating the primary adhesive web, the transfer adhesive web, and the mask transfer liner together at a single nip roll. The mask transfer liner was sandwiched between the primary adhesive web and the transfer adhesive web so that the antimicrobial adhesive on the transfer adhesive web transferred through the voids in the mask transfer liner and adhered as adhesive islands along the center of the adhesive side of the primary adhesive web.

The mask transfer liner was positioned so that the silicone-treated side faced the primary adhesive web and the untreated side faced the transfer adhesive web. The primary adhesive web (now having a series of antimicrobial adhesive islands) was then laminated on the adhesive side to a product release liner made of bleached, one-side polyethylene and then silicone coated, one-side untreated, Kraft paper to form a composite web.

The composite web with both adhesives located thereon was then converted into final medical dressings as described in Example 1 of U.S. Pat. No. 5,531,855 (Heinecke, et al.). Briefly, carrier material was die cut to form windows that were then removed. The carrier material was heat laminated to the film side of the composite web and the resulting web was cut into the required dressing size using rotary equipment.

EXAMPLE 3

Medical Dressing Preparation Using Mask Transfer Liner

A medical dressing was prepared as described in Example 2, except that the mask transfer liner was bleached, two-side silicone coated, differential release Kraft paper. The liner was positioned so that the "tight side" of the differential release mask transfer liner faced the transfer adhesive web.

EXAMPLE 4

Medical Dressing Preparation Using Mask Transfer Liner

A medical dressing was prepared as described in Example 3, except that the antimicrobial adhesive was coated at 33 g/m² on the transfer adhesive web.

EXAMPLES 5–7

Medical Dressing Preparation Using Mask Transfer Liner

Medical dressings were prepared as described in Example 3, except that the antimicrobial adhesive was coated at either 10 g/m² (Example 5), 17 g/m² (Example 6), or 33 g/m² (Example 7) on the transfer adhesive web.

Patents, patent applications, and publications disclosed herein are hereby incorporated by reference in their entirety as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

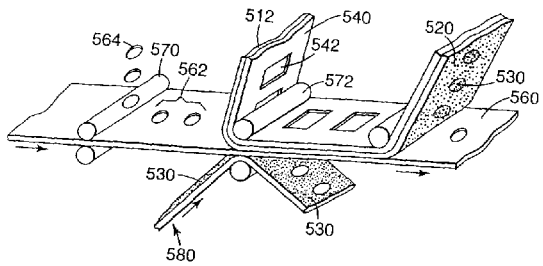

What is claimed is:

1. A method of transferring an adhesive to a substrate comprising:
   providing a mask liner comprising a plurality of voids formed therein;
   locating a receiving surface proximate a first side of the mask liner, wherein a portion of the receiving surface is exposed through at least one void of the plurality of voids in the mask liner;
   providing transfer adhesive on a transfer liner; and
   transferring at least a portion of the transfer adhesive to the portion of the receiving surface exposed through the at least one void in the mask liner.

2. The method of claim 1, wherein the transferring comprises laminating the receiving surface, mask liner, transfer adhesive, and transfer liner together, and wherein the receiving surface contacts the transfer adhesive through the at least one void.

3. The method of claim 1, wherein the transfer adhesive is substantially continuous over a release surface of the transfer liner.

4. The method of claim 1, wherein the receiving surface comprises a first adhesive, and further wherein a major surface of the mask liner facing the first adhesive comprises a release coating.

5. The method of claim 4, wherein the transfer adhesive is located on the first adhesive.

6. The method of claim 4, wherein the transfer adhesive is in direct contact with the receiving surface.

7. The method of claim 4, wherein a major surface of the mask liner facing the transfer adhesive is substantially free of a release coating.

8. The method of claim 1, wherein the transfer liner, mask liner and receiving surface each comprise a substantially continuous web, and further wherein the transferring comprises laminating the receiving surface, mask liner, transfer adhesive, and transfer liner together in a nip, whereby the receiving surface contacts the transfer adhesive through the plurality of voids in the mask liner.

9. The method of claim 8, wherein the transfer adhesive is substantially continuous over a release surface of the transfer liner.

10. The method of claim 8, wherein the receiving surface comprises a first adhesive, and further wherein a major surface of the mask liner facing the first adhesive comprises a release coating.

11. The method of claim 10, wherein a major surface of the mask liner facing the transfer adhesive is substantially free of a release coating.

12. A method of transferring an adhesive to a medical dressing comprising:
    providing a mask liner comprising a plurality of voids formed therein;
    locating a receiving surface proximate a first side of the mask liner, wherein a portion of the receiving surface is exposed through at least one void of the plurality of voids in the mask liner;
    providing transfer adhesive on a transfer liner; and
    transferring at least a portion of the transfer adhesive to the portion of the receiving surface exposed through the at least one void in the mask liner.

13. The method of claim 12, wherein the transferring comprises laminating the receiving surface, mask liner, transfer adhesive, and transfer liner together, and wherein the receiving surface contacts the transfer adhesive through the at least one void.

14. The method of claim 12, wherein the transfer adhesive is substantially continuous over a release surface of the transfer liner.

15. The method of claim 12, wherein the receiving surface comprises a first adhesive, and further wherein a major surface of the mask liner facing the first adhesive comprises a release coating.

16. The method of claim 15, wherein the transfer adhesive is located on the first adhesive.

17. The method of claim 15, wherein the transfer adhesive is in direct contact with the receiving surface.

18. The method of claim 15, wherein a major surface of the mask liner facing the transfer adhesive is substantially free of a release coating.

19. The method of claim 12, wherein the transfer liner, mask liner and receiving surface each comprise a substantially continuous web, and further wherein the transferring comprises laminating the receiving surface, mask liner, transfer adhesive, and transfer liner together in a nip, whereby the receiving surface contacts the transfer adhesive through the at least one void in the mask liner.

20. The method of claim 19, wherein the transfer adhesive is substantially continuous over a release surface of the transfer liner.

21. The method of claim 19, wherein the receiving surface comprises a first adhesive, and further wherein a major surface of the mask liner facing the first adhesive comprises a release coating.

22. The method of claim 21, wherein a major surface of the mask liner facing the transfer adhesive is substantially free of a release coating.

23. A method of manufacturing a medical dressing, comprising:
   providing a mask liner comprising a plurality of voids formed therein;
   providing a medical dressing backing comprising a receiving surface on a first major side of the medical dressing backing, wherein the receiving surface comprises a backing adhesive;
   locating the receiving surface proximate a first major side of the mask liner, wherein a portion of the receiving surface is exposed through at least one void of the plurality of voids in the mask liner;
   providing transfer adhesive on a transfer liner; and
   transferring at least a portion of the transfer adhesive to the portion of the receiving surface exposed through the at least one void in the mask liner.

24. The method of claim 23, wherein the transfer adhesive is located on the backing adhesive.

25. The method of claim 23, wherein the transfer adhesive is in direct contact with the medical dressing backing.

26. The method of claim 23, wherein the medical dressing backing comprises a second major surface, and further wherein a carrier layer is attached to the second major surface of the medical dressing backing.

27. The method of claim 23, wherein the carrier layer comprises a plurality of windows formed therein.

28. The method of claim 23, wherein the transferring comprises laminating the backing, backing adhesive, mask liner, transfer adhesive, and transfer liner together, and wherein the receiving surface contacts the transfer adhesive through the at least one void in the mask liner.

29. The method of claim 23 further comprising:
   providing a product liner; and
   laminating the backing, backing adhesive, transfer adhesive, and product liner together.

30. The method of claim 29, wherein the backing and product liner each comprise a substantially continuous web.

31. The method of claim 30 further comprising separating the substantially continuous web into individual dressings.

32. The method of claim 23, wherein the transfer adhesive is substantially continuous over a release surface of the transfer liner.

33. The method of claim 23, wherein the first major surface of the mask liner comprises a release coating.

34. The method of claim 33, wherein the mask liner further comprises a second major surface that faces the transfer adhesive, and further wherein the second major surface of the mask liner is substantially free of the release coating.

35. The method of claim 23, wherein the backing adhesive has a higher tack to skin than the transfer adhesive.

36. The method of claim 23, wherein the transfer adhesive comprises at least one bioactive agent and is substantially contact transparent.

37. The method of claim 23, wherein the backing adhesive forms a border around a perimeter of the receiving surface.

* * * * *

UNITED STATES PATENT AND TRADEMARK OFFICE
CERTIFICATE OF CORRECTION

PATENT NO. : 6,461,467 B2
DATED : October 8, 2002
INVENTOR(S) : Todd A. Blatchford et al.

It is certified that error appears in the above-identified patent and that said Letters Patent is hereby corrected as shown below:

The title page, should be deleted and substitute therefore the attached title page as shown on the attached page.

Delete drawings sheets 1, 3 and 4 and asubstitute therefore drawings sheets 1, 3 and 4 consisting of Figs. 3, 6 and 7 as shown on the attached pages.

Title page,
Item [56], References Cited, FOREIGN PATENT DOCUMENTS, please add:

-- EP     0 353 972    7/1989
       WO    99/00080    1/1999 --

Signed and Sealed this

Fourteenth Day of September, 2004

JON W. DUDAS
*Director of the United States Patent and Trademark Office*

(12) United States Patent
Blatchford et al.

(10) Patent No.: US 6,461,467 B2
(45) Date of Patent: Oct. 8, 2002

(54) MEDICAL DRESSINGS WITH MULTIPLE ADHESIVES AND METHODS OF MANUFACTURING

(75) Inventors: Todd A. Blatchford, Woodbury, MN (US); Steven B. Heinecke, New Richmond, WI (US); Donald H. Lucast, North St. Paul; Donald G. Peterson, Shoreview, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/840,405

(22) Filed: Apr. 23, 2001

(65) Prior Publication Data

US 2001/0051178 A1 Dec. 13, 2001

Related U.S. Application Data

(62) Division of application No. 09/524,139, filed on Mar. 10, 2000.

(51) Int. Cl.$^7$ .................... B44C 3/02; B32B 31/20; B05D 1/32; A61L 15/58; A61F 13/02
(52) U.S. Cl. .......... 156/230; 156/234; 156/240; 156/241; 156/247; 156/250; 156/289; 156/293; 427/2.31; 427/282; 428/42.3; 428/195; 428/914; 424/445; 424/448; 602/43; 602/55; 602/58
(58) Field of Search .................... 156/230, 234, 156/235, 240, 241, 247, 250, 289, 293, 298; 427/2.21, 2.31, 272, 282, 146; 428/41.8, 41.9, 42.3, 195, 202, 914, 343; 424/443, 445, 448; 602/43, 55, 57, 58

(56) References Cited

U.S. PATENT DOCUMENTS

| | | |
|---|---|---|
| 1,280,631 A | 10/1918 | Atkinson |
| RE24,906 E | 12/1960 | Ulrich |
| 3,389,827 A | 6/1968 | Abere et al. |

(List continued on next page.)

FOREIGN PATENT DOCUMENTS

| | | |
|---|---|---|
| EP | 0 035 399 B1 | 2/1985 |
| EP | 0 051 935 B1 | 11/1986 |

(List continued on next page.)

OTHER PUBLICATIONS

Satas, D., Ed., *Handbook of Pressure Sensitive Adhesive Technology*, Ch. 18, Van Nostrand Reinhold Co., Title Page, Publication Page, Table of Contents, and pp. 384–403 (1982).

*Primary Examiner*—J. A. Lorengo
(74) *Attorney, Agent, or Firm*—John A. Burtis

(57) ABSTRACT

Medical dressings are disclosed that include multiple exposed pressure sensitive adhesives. One of the pressure sensitive adhesives includes a bioactive agent and is substantially contact transparent. In some embodiments, all of the adhesives are substantially contact transparent. Also provided are methods of manufacturing the medical dressings. By providing multiple exposed pressure sensitive adhesives, the pressure sensitive adhesive formulations can be varied to provide desired properties in different areas of the dressing. A pressure sensitive adhesive that exhibits relatively high tack to skin may be provided around the periphery of the dressing while a pressure sensitive adhesive incorporating a bioactive agent is provided in the center of the dressing. Alternatively, a higher tack pressure sensitive adhesive may be provided at two opposing sides of the dressing with a bioactive adhesive located in between the opposing portions of higher tack adhesive. The present invention also provides methods of transferring adhesives using a mask such that the adhesive is transferred to selected areas of a receiving surface. The mask may be provided in the form of a liner including a plurality of voids formed therein.

37 Claims, 4 Drawing Sheets